United States Patent
Lee et al.

(10) Patent No.: US 9,914,685 B2
(45) Date of Patent: *Mar. 13, 2018

(54) SYSTEM FOR REMOVING SALT FROM A RICH MONO ETHYLENE GLYCOL STREAM

(71) Applicant: Cameron Solutions, Inc., Houston, TX (US)

(72) Inventors: Joseph Min-Hsiun Lee, Houston, TX (US); Gary W. Sams, Spring, TX (US)

(73) Assignee: Cameron Solutions, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/376,066

(22) Filed: Dec. 12, 2016

(65) Prior Publication Data

US 2017/0233317 A1   Aug. 17, 2017

Related U.S. Application Data

(63) Continuation of application No. 14/874,724, filed on Oct. 5, 2015, now Pat. No. 9,522,865, which is a continuation of application No. 14/307,217, filed on Jun. 17, 2014, now Pat. No. 9,150,477.

(51) Int. Cl.
  *C07C 29/76* (2006.01)
  *C07C 29/80* (2006.01)
  *B01D 3/14* (2006.01)
  *B01D 3/06* (2006.01)
  *B01D 21/26* (2006.01)

(52) U.S. Cl.
  CPC .............. *C07C 29/76* (2013.01); *B01D 3/06* (2013.01); *B01D 3/143* (2013.01); *B01D 21/267* (2013.01); *C07C 29/80* (2013.01)

(58) Field of Classification Search
  CPC .......... C07C 29/76; C07C 29/80; B01D 3/14; B01D 21/26

USPC ........................................................ 568/868
See application file for complete search history.

(56) References Cited

U.S. PATENT DOCUMENTS

| | | | |
|---|---|---|---|
| 9,150,477 B1 * | 10/2015 | Lee | C07C 29/76 |
| 9,522,865 B2 * | 12/2016 | Lee | C07C 29/76 |
| 2003/0118989 A1 * | 6/2003 | Rosenow | C12N 1/06 |
| | | | 435/6.14 |

FOREIGN PATENT DOCUMENTS

| | | |
|---|---|---|
| WO | 2007073204 A1 | 6/2007 |
| WO | 2009017971 A1 | 2/2009 |
| WO | 2010080038 A1 | 7/2010 |
| WO | 2013074183 A1 | 5/2013 |

OTHER PUBLICATIONS

Cameron: "Puremeg—MEG reclamation and regeneration technology" Jan. 1, 2013.

* cited by examiner

*Primary Examiner* — Yong Chu
(74) *Attorney, Agent, or Firm* — Gable Gotwals

(57) ABSTRACT

A system for, and method of, recovering salt from fluid stream in a recycle loop of a flash separator has a desanding hydrocyclone located in the hot recycle loop of the flash separator; a first solids fluidization device located at the bottom end of the flash separator's brine column; a second desanding hydrocyclone arranged to receive a salt slurry stream created by the first solids fluidization device; and an accumulator located downstream of the second desanding hydrocyclone and having a second solids fluidization device located at its bottom end. Each solids fluidization device causes a motive fluid to exit the device in a swirling motion to fluidize the salt components contained in the resident fluid. The overflow from the second desanding hydrocyclone is the motive fluid for the brine column and a produced water, condensate water, or seawater stream is the motive fluid for the accumulator.

17 Claims, 3 Drawing Sheets

SYSTEM FOR REMOVING SALT FROM A RICH MONO ETHYLENE GLYCOL STREAM

CROSS REFERENCE TO RELATED APPLICATIONS

This application is a continuation application of U.S. patent application Ser. No. 14/874,724, filed Oct. 5, 2015, now U.S. Pat. No. 9,522,865, which was a continuation application of U.S. patent application Ser. No. 14/307,217, filed Jun. 17, 2014, now U.S. Pat. No. 9,150,477, the contents of which are hereby incorporated by reference in their entirety.

BACKGROUND

This disclosure relates to processes designed to treat mono ethylene glycol (MEG) used in the oil and gas industry, especially in offshore locations, to control hydrates formation. More particularly, the disclosure relates to MEG reclamation processes which are designed to remove salts and other contaminants from a wet MEG feed stream.

In the oil and gas industry, dry (lean) MEG is used to control the formation of hydrates within the produced stream. The now wet (rich) MEG is, in turn, dried by way of a MEG reclamation process so the MEG can be used again in hydrate control.

The unit used to recover MEG usually includes three sections: pre-treatment, flash separation, and MEG regeneration. Those sections can be followed by salt management and calcium removal sections.

In the pre-treatment stage, the rich MEG containing some dissolved gas and hydrocarbon liquids must pass through a three-phase separator vessel. The gas is flashed and recovered hydrocarbon liquids are sent to the production separator. The rich MEG is sent to a flash separator. The rich MEG stream comprised of produced water and MEG is fed to the flash separator where it is brought into contact with a hot recycle stream of MEG. The flash separator operates under vacuum. The MEG and water components of the rich MEG stream are flashed and exit through the top of the flash separator where they are sent to the MEG distillation column for regeneration. The salt components of the rich MEG stream precipitate in the flash separator.

The MEG regeneration section is a refluxed distillation column. The distillation column also operates under vacuum and distills the water from the MEG-water vapors coming off the top of the flash separator. Salt-free, lean MEG produced at the bottom of the distillation column is pumped to storage for reuse. The vaporized water passes overhead from the distillation column. The water is condensed and collected in the reflux drum. A small amount is returned to the distillation column as reflux, and the remaining is routed to treatment.

The salt crystals that precipitate in the flash separator are separated by gravity to the bottom of the brine column, where they are transferred to the salt tank. There, the salts are concentrated before removal through a centrifuge.

The salts in produced water cover a variety of species, but generally are categorized into monovalent salts (typically sodium and potassium), and divalent salts (typically calcium and magnesium). The divalent salts cannot be effectively precipitated in the same manner as the monovalent salts, so a separate calcium removal process may be installed. Effective calcium control is accomplished as the divalent salts are collected, reacted and removed through a centrifuge with the centrate overflow returning to the process.

Current methods of removing the salt crystals from the bottom of the brine column involve a lot of equipment, including but not limited to complicated and expensive centrifugal, centrifuge pump filtration systems, a salt tank, a centrate tank, and a density measurement device. Reducing the footprint of the system for removing the salt crystals and other contaminants is important for making more efficient use of space, reducing off-shore construction costs, and increasing ease of system operation and maintenance.

SUMMARY

A system for removing salt from a fluid stream may include a first solids fluidization device and a first removal device. The first solids fluidization device is arranged at the lower end of the fluid column of a flash separator, is in communication with a first motive fluid stream, and includes means for causing the first motive fluid stream to swirl when exiting the device. The first removal device is located above the first solids fluidization device and is arranged to carry a first salt slurry stream created by the first solids fluidization device away from the fluid column to a hydrocyclone located outside of the fluid column.

A method of removing salt from a fluid stream may include introducing a first swirling motive fluid stream into the bottom end of the fluid column of a flash separator to form a first salt slurry stream. The first salt slurry stream then passes to a hydrocyclone located outside of the flash separator.

Embodiments of this disclosure may (1) remove salt without complicated and expensive centrifugal filters; (2) eliminate centrifuge filtration, a salt tank, a centrate tank, and density measurement devices; and (3) have less foot print than the prior art systems and methods and have lower construction costs and be easier to operate and maintain than those prior art systems and methods.

BRIEF DESCRIPTION OF THE DRAWINGS

So that the manner in which the above recited features can be understood in detail, a more particular description may be had by reference to the embodiments, some of which are illustrated in the appended drawings, wherein like reference numerals denote like elements. It is to be noted, however, that the appended drawings illustrate various embodiments and are therefore not to be considered limited of its scope, and may admit to other equally effective embodiments.

ELEMENTS AND NUMBERING USED IN THE DRAWINGS

Figure 1:
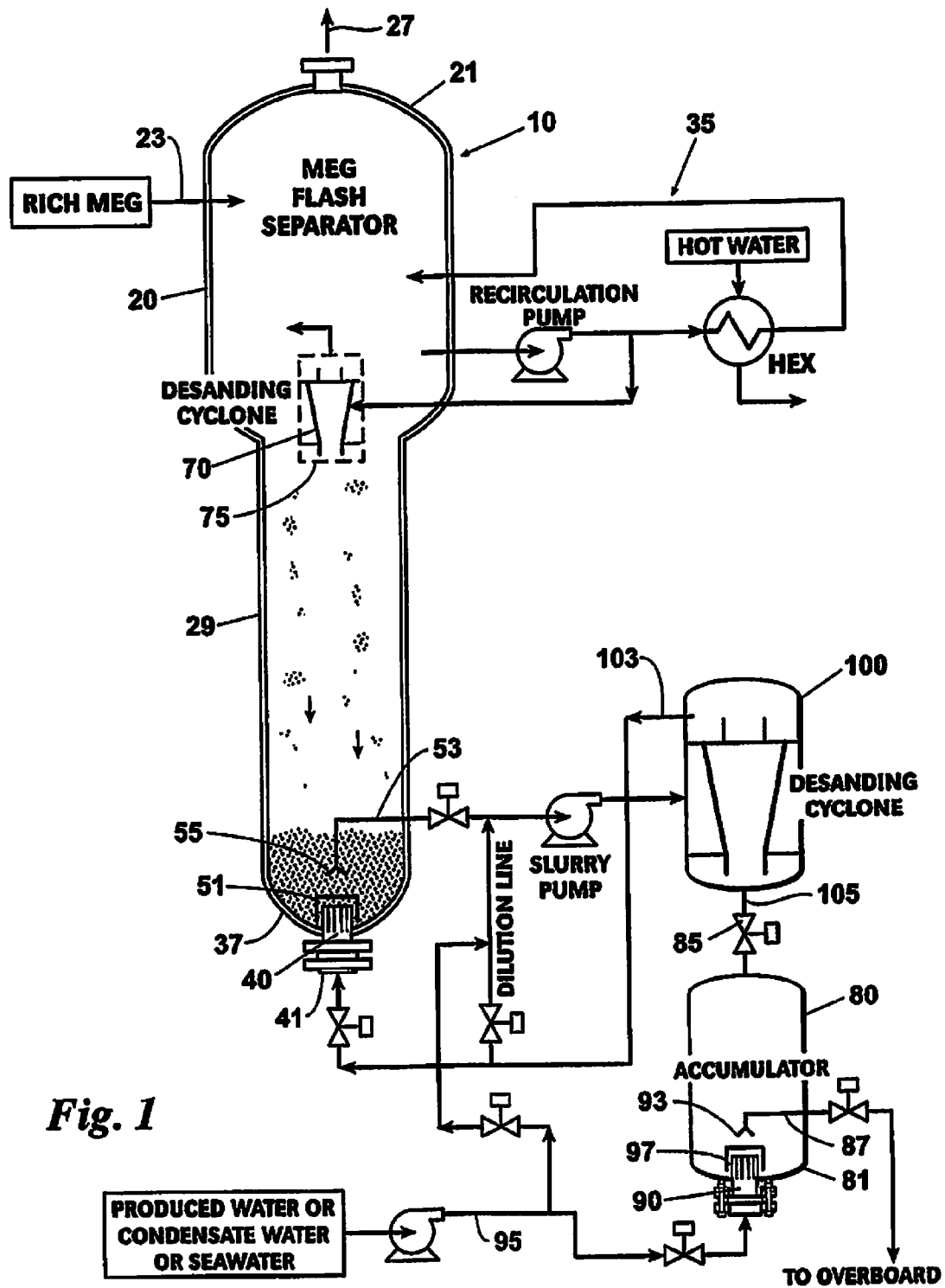
FIG. 1 is a schematic of an embodiment of the MEG recovery system and process. The system includes two desanding hydrocyclones and two solids fluidization devices.
Figure 3:
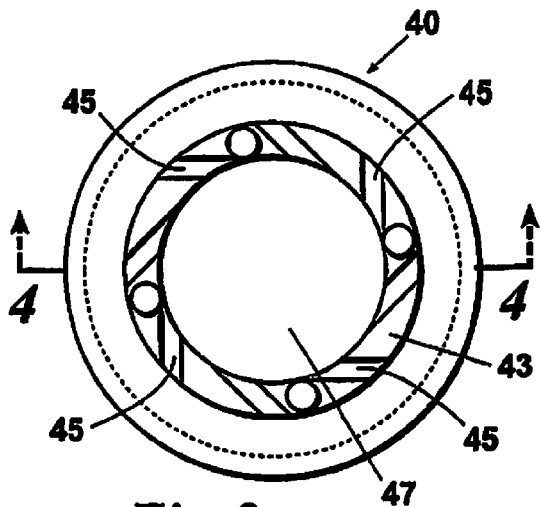
FIG. 3 is top view of the solids fluidization device of FIG. 2.
Figure 5:
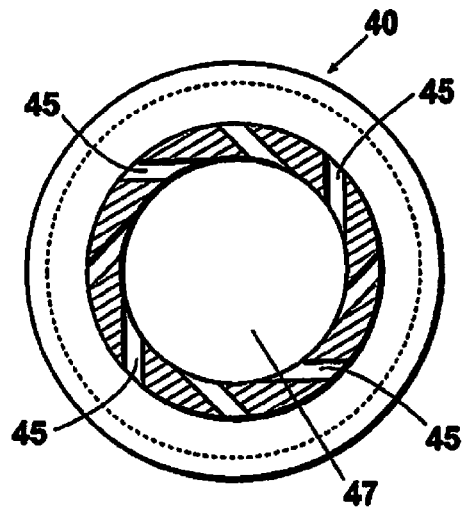
FIG. 5 is a cross-section view of the solids fluidization device of FIG. 2 taken along section line 5-5 of FIG. 2.
Figure 2:
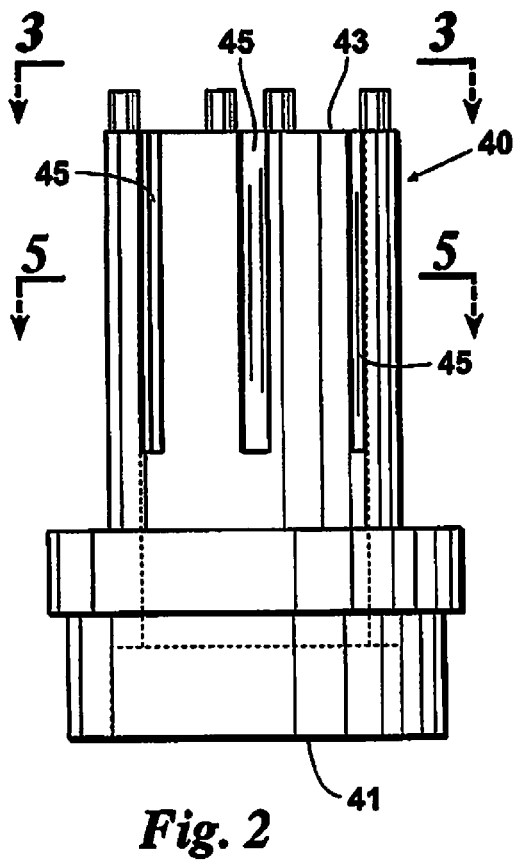
FIG. 2 is a front elevation view of the embodiment of the solids fluidization device of FIG. 1.
Figure 4:
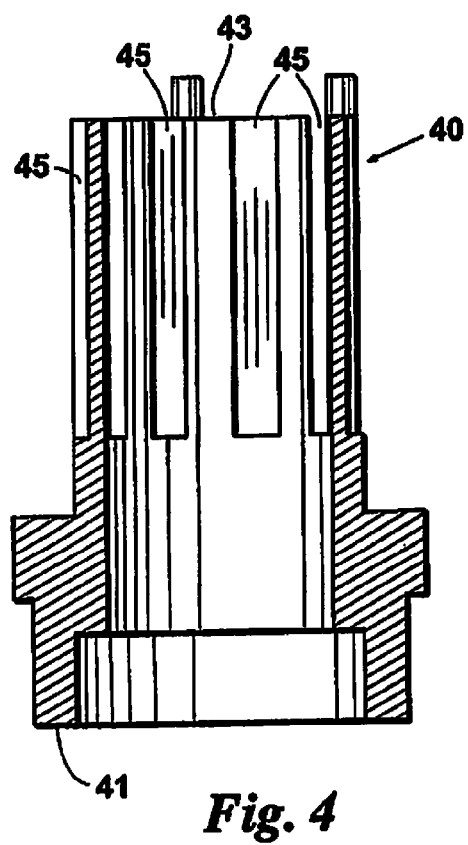
FIG. 4 is a cross-section view of the solids fluidization device of FIG. 2.

10 MEG recovery system
20 Flash separator

21 Upper end
23 Rich (wet) MEG stream
27 Water and MEG vapor stream
29 Brine or downcomer column or section
35 Hot MEG recycle stream or recycle (recirculation) loop
37 Bottom end
40 First solids fluidization device
41 Inlet or lower inlet end
43 Upper end of 40
45 Slots of 40
47 Central or inner bore
51 First swirling motive fluid stream
53 First salt slurry (discharge) stream
55 First removal device
70 First desanding hydrocyclone
75 Underflow end or stream
80 Accumulator
81 Bottom end
85 Valve
87 Second salt slurry (discharge) stream
90 Second solids fluidization device
93 Second removal device
95 Produced water, condensate water. or seawater (carrier or motive fluid) stream
97 Second swirling motive fluid stream
100 Second desanding hydrocyclone
103 Overflow end or stream
105 Underflow end or stream

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims, the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream", "above" and "below", and other like terms indicating relative positions above or below a given point or element are used in this description to more clearly describe some embodiments of the disclosure.

Figure 6:
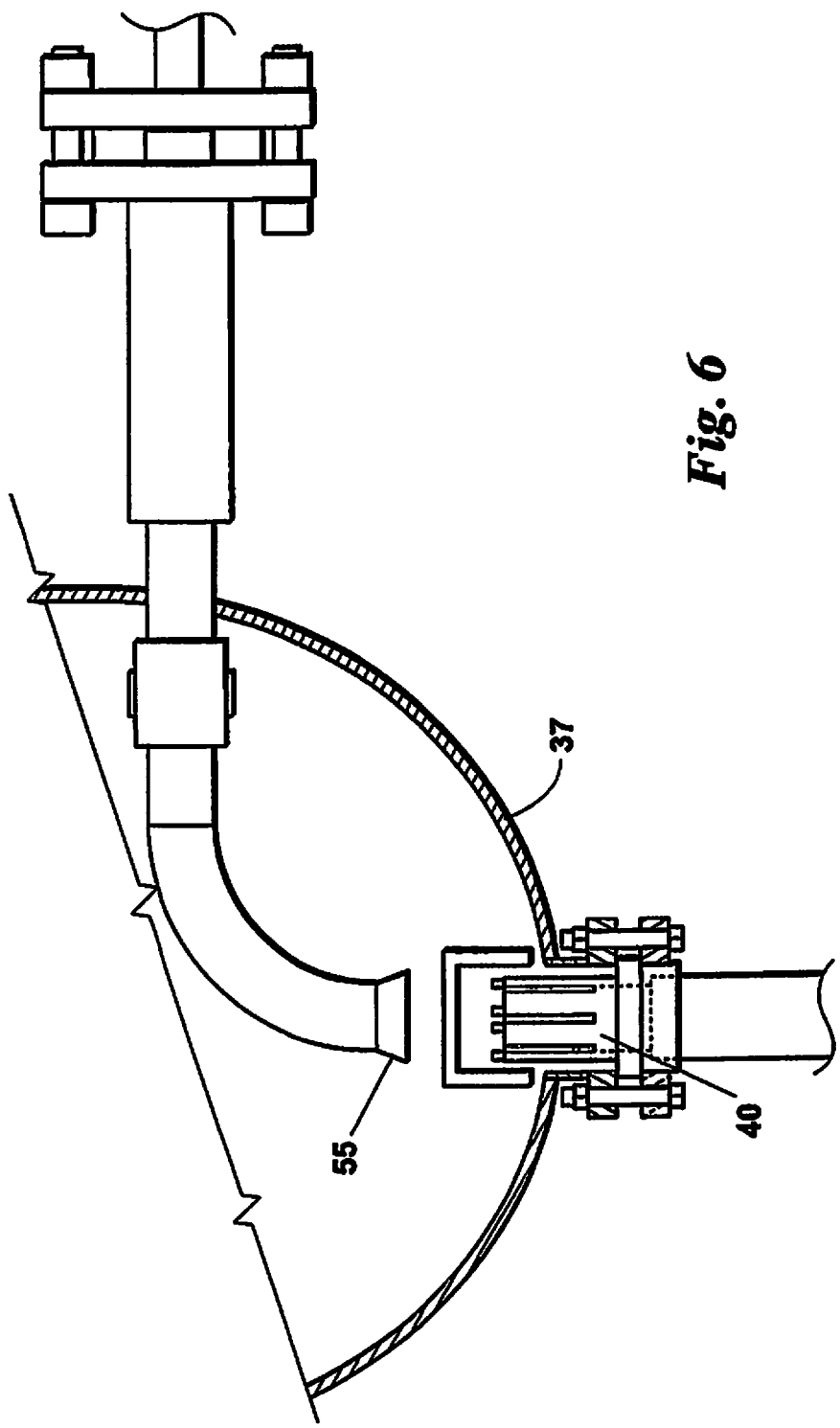
FIG. 6 is an enlarged view of the solids fluidization devices of FIG. 1 and the removal device located directly above each of the solids fluidization devices.

Referring first to FIGS. 1 and 6, an embodiment of a MEG recovery system 10 for a MEG process includes (1) a flash separator 20 having a desanding hydrocyclone 70 located in the hot MEG recycle stream or loop 35 of the separator 20; (2) a solids fluidization device 40 located at the bottom end 37 of the brine column 29; (3) a second desanding hydrocyclone 100 arranged to receive a first salt slurry stream 53 exiting the brine column 29; and (4) an accumulator 80 arranged to receive an underflow stream 105 of the second desanding hydrocyclone 100 and having a second solids fluidization device 90 for producing a second salt slurry stream 87.

Flash separator 20 is of a kind well known in the art. In the separator 20 a rich (wet) MEG inlet stream 23 is brought into contact with a hot MEG recycle loop 35. The MEG and water components of the rich MEG stream 23 are flashed and exit the upper end 21 of the separator 20 as a water and MEG vapor stream 27. The salt components 27 of the rich MEG inlet stream 23 precipitate in the brine column 29 of the separator 20. A MEG/brine transition zone (not shown) can form in the column between the MEG and the brine, but the desanding hydrocyclone 70 facilitates the settling of salt into the brine column 29 and, therefore, helps prevent salt from rising up in the column and negatively affecting the performance of the separator 20.

The desanding hydrocyclone 70 of flash separator 20 reduces the salt concentration in the heat exchanger of the recycle loop 35 by removing salt particles in the stream diverted from the loop 35 and introduced to the desanding hydrocyclone 70. A small portion (which may be less than about 10%) of the total recirculation pump flow rate may be introduced into the desanding hydrocyclone 70. The underflow stream 75 from the desanding hydrocyclone 70 enters the brine or downcomer column 29 of the flash separator 20. A MOZLEY® desanding hydrocyclone (Cameron Process Systems, Houston, Tex.) is a suitable desanding hydrocyclone 70.

Solids fluidization device 40 is arranged at the bottom end 37 of the column 29. The device 40 includes means which produce or cause a swirling (e.g. vertiginous, rotary or cyclonic) motion or flow 51 of the motive fluid as it exits device 40. One suitable device 40 is a HYDROTRANS™ solids fluidization and removal device (Cameron Process Systems, Houston, Tex). Any other device may be used as the fluidization device provided the device creates a swirling (e.g., vertiginous, rotating, or cyclonic) motive fluid flow when the flow exits the device.

Referring to FIGS. 2-5, the HYDROTRANS™ device includes a plurality of spaced-apart slots 45 arranged tangential to, surrounding, and in communication with an inner bore 47 which receives a motive fluid stream 103 at the lower inlet end 41 of the device. Motive fluid steam 103—which comes from the overflow end of the second desanding hydrocyclone 100—exits the slots 45 of device 40 as a swirling motive fluid stream 51. The swirling motion of the motive fluid stream 51 mixes with the solid/salt already residing in the bottom of column 29 to fluidize the salt, thereby creating a salt slurry stream 53.

Unlike the desanding hydrocyclones 70, 100—which produce a cyclonic flow within the device but a straight over- and underflow exiting the device (L e., straight in, cyclonic within, and straight out)—the solids fluidization device 40 (and 90) produces this type of flow external to the device (i.e., straight in and rotary or cyclonic out).

A removal device 55, which can be a slurry discharge head, resides just above the upper end 43 of solids fluidization device 40. Removal device 55 carries the salt slurry stream 53 to the second desanding hydrocyclone 100. Prior to entering the second desanding hydrocyclone, the salt slurry stream 53 can be diluted with a produced water, condensate water, or seawater stream 95 (or some combination thereof). The solids separated in the hydrocyclone 100 exit as an underflow stream 105 and are passed to an accumulator 80; the overflow stream 103 is passed back to solids fluidization device 40. When the salt level in the accumulator 80 reaches a predetermined height, which may be about 50% of the accumulator's height, the valve 85 located between the desanding hydrocyclone 100 and the accumulator 80 should be closed.

Removing the salt from the accumulator 80 occurs in the same manner as does removing the salt from the brine column 29. A solids fluidization device 90, the same or similar to that of solids fluidization device 40, is arranged at the bottom end 81 of the accumulator 80. A produced water, condensate water, or seawater stream 95 (or some combination thereof) enters the device 90 and is converted into a swirling motive fluid stream 97 which fluidizes the salt components residing in the accumulator 80 and creates a salt slurry 87.

A removal device 93, which can be a slurry discharge head, resides just above solids fluidization device 90. Removal device 93 carries the salt slurry stream 87 away from the accumulator 80, where it can be discharged overboard.

A method of removing salt from a rich MEG stream which makes use of system 10 includes:
i. passing a portion of the hot MEG stream in the recycle or recirculation loop 35 of the flash separator 20 to a desanding hydrocyclone 70 located in the recycle or recirculation loop 35;
ii. introducing a swirling motive fluid stream 51 into the bottom end 37 of the brine column to form a first salt slurry stream 53;
iii. pumping the first salt slurry stream 53 to a second desanding hydrocyclone 100;
iv. closing a valve 85 located between the desanding hydrocyclone 100 and the accumulator 80; and
v. introducing a swirling motive fluid stream 97 into the bottom end 81 of the accumulator 80 to form a second salt slurry (discharge) stream 87.

A small portion (which may be less than about 10%) of the total recirculation pump flow rate should be introduced into the desanding hydrocyclone 70 located in the recycle or recirculation loop 35 of the flash separator 20 when the portion of the hot MEG stream in the recycle or recirculation loop 35 is passed to the desanding hydrocyclone 70. The valve 85 should be closed when the salt level is at about 50% of the accumulator height.

The method may also include diluting the first salt slurry stream 53 with a produced water, condensate water, or seawater stream 99 prior to it entering the second desanding hydrocyclone 100 to prevent plugging by high solid concentration. An overflow stream 103 from the second desanding hydrocyclone 100 may be used as the source for the swirling motive fluid stream 51. A produced water, condensate water, or salt water stream 95 can be used as the source for swirling motive fluid stream 97. The swirling motive fluid streams 51, 97 may be produced by solids fluidization devices 40, 90, respectively, or any device that produces a swirling motive fluid flow upon the flow exiting the device.

The prior art makes use of complicated and expensive centrifugal filters to remove salt, along with centrifuge filtration, a salt tank, a centrate tank, and density measurement devices, none of which are present in system 10 and the method for its use. System 10 also occupies less foot print than the prior art systems and methods, has lower construction costs, and is easier to operate and maintain than those prior art systems.

While systems and methods for removing salt from a fluid stream have been described with a certain degree of particularity, many changes may be made in the details of construction and the arrangement of components and steps without departing from the spirit and scope of this disclosure. Systems and methods according to this disclosure, therefore, are limited only by the scope of the attached claims, including the full range of equivalency to which each element thereof is entitled.

What is claimed is:

1. A system for removing salt from a fluid stream, the system comprising:
    a first solids fluidization device arranged at a lower end of a fluid column of a flash separator and in communication with a first motive fluid stream, the first solids fluidization device including means for causing the first motive fluid stream to swirl when exiting the first solids fluidization device; and
    a first removal device located above the first solids fluidization device and arranged to carry a first salt slurry stream created by the first solids fluidization device away from the fluid column to a hydrocyclone located outside of the fluid column.

2. A system according to claim 1 further comprising an accumulator arranged to receive an underflow stream of the hydrocyclone located outside of the fluid column.

3. A system according to claim 2 further comprising a shut-off valve located between the hydrocyclone located outside of the fluid column and the accumulator.

4. A system according to claim 2 further comprising the accumulator including a second solids fluidization device arranged at a lower end of the accumulator in communication with a second motive fluid stream.

5. A system according to claim 4 wherein the second solids fluidization device includes a plurality of spaced-apart vertical slots arranged tangential to and surrounding a central bore of the second solids fluidization device.

6. A system according to claim 4 wherein a source of the second motive fluid stream is at least one of a produced water, condensate water, or seawater stream.

7. A system according to claim 1 wherein an overflow of the hydrocyclone located outside of the fluid column is a source of the first motive fluid stream.

8. A system according to claim 1 wherein the first salt slurry stream is diluted with at least one of a produced water, condensate water, or seawater stream.

9. A system according to claim 1 wherein the first solids fluidization device includes a plurality of spaced-apart vertical slots arranged tangential to and surrounding a central bore of the first solids fluidization device.

10. A method of removing salt from a fluid stream, the method comprising:
    i. introducing a first swirling motive fluid stream into a bottom end of a fluid column of a flash separator to form a first salt slurry stream; and
    ii. passing the first salt slurry stream to a hydrocyclone located outside of the flash separator.

11. A method according to claim 10 wherein a source of the first swirling motive fluid stream is an overflow stream of the hydrocyclone located outside of the flash separator.

12. A method according to claim 10 further comprising diluting the first salt slurry stream with at least one of a produced water stream, a condensate water stream, and a seawater stream prior to it entering the hydrocyclone located outside of the flash separator.

13. A method according to claim 10 further comprising:
    passing an underflow stream from the hydrocyclone located outside of the flash separator to an accumulator; and
    introducing a second swirling motive fluid stream into a bottom end of the accumulator to form a second salt slurry stream.

14. A method according to claim 13 further comprising closing a valve located between the hydrocyclone located outside of the flash separator and the accumulator when a salt level within the accumulator is at a predetermined height of the accumulator.

15. A method according to claim 13 wherein a source of the second swirling motive fluid stream is at least one of a produced water stream, a condensate stream, and a salt water stream.

16. A system according to claim 1 wherein a hydrocyclone located in a recirculation loop of the flash separator is arranged so an underflow of the hydrocyclone is introduced into the fluid column of the flash separator.

17. A method according to claim 10 further comprising passing a portion of a recirculation loop stream to a hydrocyclone located within the flash separator.

* * * * *